(12) United States Patent
Pagani et al.

(10) Patent No.: US 6,696,026 B2
(45) Date of Patent: Feb. 24, 2004

(54) PROCESS FOR COMBINED PRODUCTION OF AMMONIA AND UREA

(75) Inventors: Giorgio Pagani, Lugano (IT); Umberto Zardi, Breganzona (IT)

(73) Assignee: Urea Casale, Lugano-Besso (CH)

( * ) Notice: Subject to any disclaimer, the term of this patent is extended or adjusted under 35 U.S.C. 154(b) by 0 days.

(21) Appl. No.: 09/759,347

(22) Filed: Jan. 16, 2001

(65) Prior Publication Data

US 2001/0002245 A1 May 31, 2001

Related U.S. Application Data

(62) Division of application No. 09/144,266, filed on Aug. 31, 1998, now Pat. No. 6,231,827.

(30) Foreign Application Priority Data

Sep. 20, 1997 (EP) .............................. 97202888

(51) Int. Cl.$^7$ .......................... C01C 1/00; C07C 273/00
(52) U.S. Cl. ...................... 422/148; 422/188; 422/189; 564/66; 564/67; 564/70; 564/73; 423/352
(58) Field of Search ................................ 422/148, 156, 422/188, 189, 193, 195, 197; 564/66, 67, 70, 71, 72, 73, 1; 423/352, 359

(56) References Cited

U.S. PATENT DOCUMENTS

| | | | |
|---|---|---|---|
| 3,310,376 A | 3/1967 | Cook et al. ................. 423/359 |
| 3,349,126 A | 10/1967 | Hau et al. ..................... 564/66 |
| 3,372,189 A | 3/1968 | Otsuka et al. ................. 564/69 |
| 4,012,443 A | 3/1977 | Bonetti ........................ 564/66 |
| 4,138,434 A | 2/1979 | Lagana et al. ............... 423/359 |
| 4,320,103 A | 3/1982 | Pagani ....................... 423/359 |
| 4,539,077 A | * 9/1985 | Jonckers et al. ............... 203/49 |
| 4,869,887 A | 9/1989 | Van Dijk ..................... 423/359 |
| 4,988,491 A | 1/1991 | Van Dijk et al. ............ 423/359 |
| 5,359,140 A | * 10/1994 | Granelli et al. ............... 564/67 |
| 5,523,483 A | * 6/1996 | Singh et al. .................. 564/68 |
| 5,849,952 A | * 12/1998 | Carloni et al. ................ 564/71 |
| 6,114,579 A | * 9/2000 | Van Wijck ................... 564/67 |

* cited by examiner

Primary Examiner—Jerry D. Johnson
Assistant Examiner—Alexa A Doroshenk
(74) Attorney, Agent, or Firm—Sughrue Mion, PLLC

(57) ABSTRACT

A process for the combined production of ammonia and urea of the type comprising an ammonia synthesis reactor (2), a urea synthesis reactor (5) and a urea recovery section (21) stands out for the fact of submitting at least a part of a flow comprising carbamate in aqueous solution coming from the urea recovery section (21) to a partial decomposition treatment, to obtain a flow comprising ammonia and carbon dioxide in vapor phase and a flow comprising diluted carbamate in aqueous solution, which is fed together with a gas flow comprising hydrogen, nitrogen and carbon dioxide, preferably obtained by hydrocarbons steam reforming, and a flow comprising ammonia coming from the ammonia synthesis reactor (2) to a carbamate synthesis section (3), where ammonia and carbon dioxide are caused to react, to obtain a flow comprising carbamate in aqueous solution and a gas flow comprising hydrogen and nitrogen. The flow comprising carbamate in aqueous solution is then sent to the urea synthesis reactor (5), while the gas flow comprising hydrogen and nitrogen is sent to the ammonia synthesis reactor (2).

17 Claims, 1 Drawing Sheet

PROCESS FOR COMBINED PRODUCTION OF AMMONIA AND UREA

Figure 1:
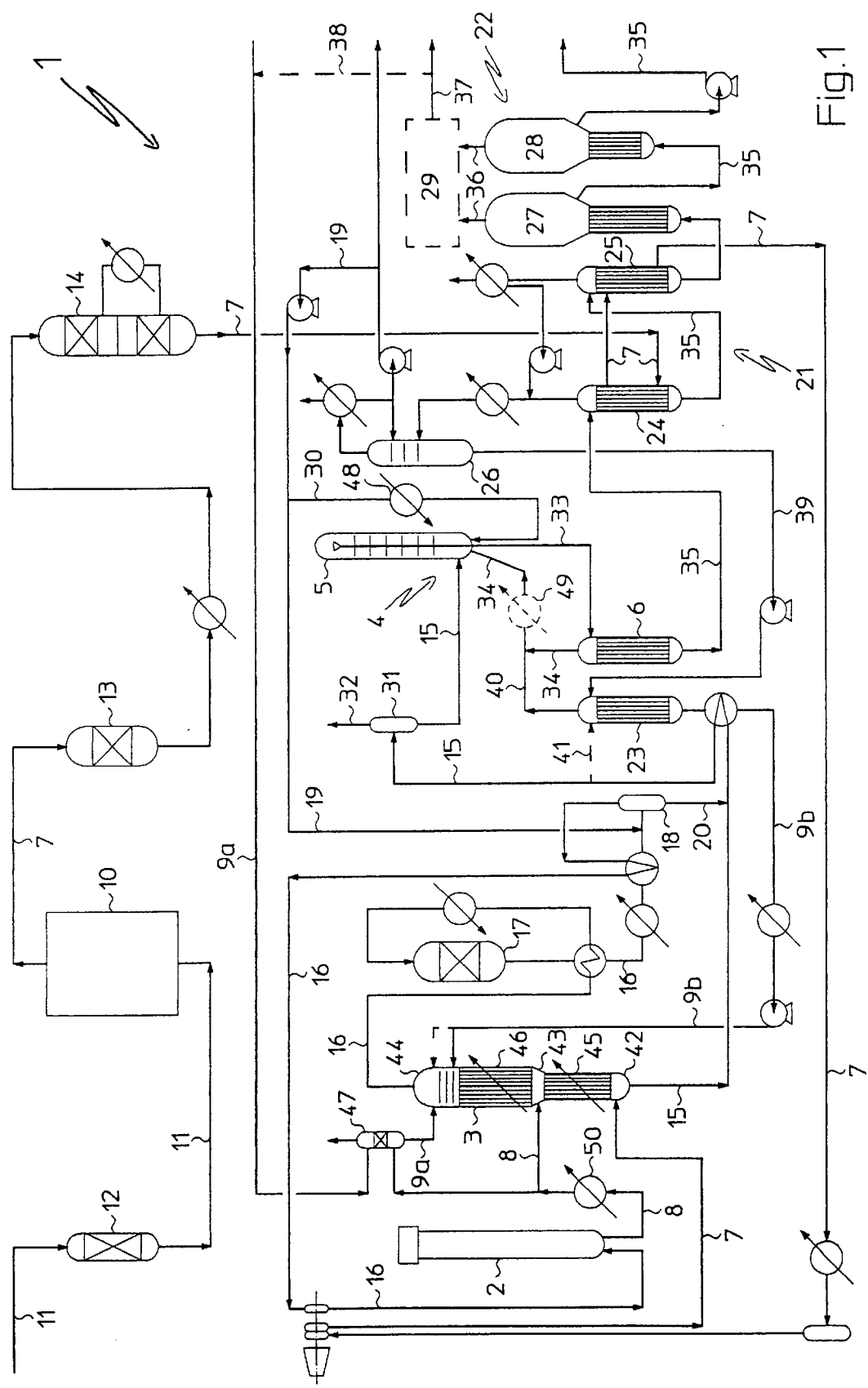

This is a divisional of application Ser. No. 09/144,266 filed Aug. 31, 1998, now U.S. Pat. No. 6,231,827, granted May 15, 2001.

FIELD OF APPLICATION

The present invention relates to a process for the combined production of ammonia and urea in a plant comprising an ammonia synthesis reactor, a urea synthesis reactor and a urea recovery section.

In the following of the description and subsequent claims, with the term: "process for the combined production of ammonia and urea", it is intended to mean a single process that integrates the ammonia production process with the urea production process.

In other words, according to this technology, urea is produced—at least in part—by causing ammonia obtained in a synthesis reactor to react with carbon dioxide contained in a synthesis raw gas flow comprising among other things hydrogen and nitrogen coming, for instance, from a reforming section. The synthesis raw gas flow, free from carbon dioxide, is thereafter sent to the ammonia synthesis reactor.

Processes of this kind allow to eliminate, or in any case, to reduce to a remarkable extent, the decarbonation section of the synthesis raw gas flow, the separation section of the ammonia produced in the corresponding synthesis reactor, and the carbon dioxide compression section. Besides, energy consumption and investment costs resulting from a single integrated system may be substantially lower than those resulting from two separate processes for ammonia and for urea.

The need to provide an integrated process is particularly felt in all cases where all or in any case most of the ammonia is converted into urea by causing it to react with carbon dioxide obtained as a by-product in the preparation of the synthesis gas.

In the following of the description and subsequent claims, with the term: "urea recovery section", it is intended to mean the part of the plant downstream of the urea synthesis reactor, comprising generally one or two carbamate decomposers at medium pressure (about 18 bar a), respectively at medium and low pressure (about 4 bar a) and related carbamate condensers, whose function is to separate the produced urea from the reaction mixture coming from the corresponding synthesis reactor, allowing in this way to obtain a 60% to 75% concentrated urea solution.

The invention also relates to a plant for implementing the aforesaid process, as well as to a method for the simultaneous modernization of an ammonia production plant and a urea production plant.

In the following of the description and subsequent claims, with the term: "simultaneous modernization", it is intended to mean a modernization that concerns—at the same time—both an existing plant for ammonia synthesis and an existing plant for urea synthesis, for the purposes of their integration.

The integration between the production processes of ammonia and urea, wherein the carbon dioxide contained in the synthesis raw gas and the synthesis ammonia are caused to react, producing a carbamate aqueous solution to be sent to the urea synthesis reactor, involves on the one hand a simplification of the plant—with special reference to the ammonia decarbonation and separation sections and to the $CO_2$ compression section—but on the other hand, a marked overloading of the sections correlated with the urea production, essentially due to the lack of formation heat and to the excessive molar ratio $H_2O/CO_2$ in the urea synthesis reactor, with an ensuing low conversion yield and high energy consumption.

As a consequence, in the field of combined production of ammonia and urea there is increasingly felt the need of providing processes allowing to increase urea conversion yield, in a simple way, with low operating and investment costs.

PRIOR ART

In order to meet the above requirement, several processes for combined production of ammonia and urea have been proposed in the field.

For instance, in U.S. Pat. Nos. 3,303,215 and 3,310,376, it is disclosed a process for the combined production according to the prior art wherein suitably purified liquid ammonia is fed to a urea synthesis reactor where ammonia is caused to react with carbon dioxide comprised in a synthesis raw gas including also hydrogen and nitrogen.

In the urea synthesis reactor, ammonia and carbon dioxide react forming ammonia carbamate which, in its turn, is transformed into urea by dehydration.

A first drawback of this process lies in that the high development of heat produced during carbamate production and the presence of inert gases (hydrogen and nitrogen) which reduce the partial pressure of ammonia and carbon dioxide makes it necessary to operate—in the urea synthesis reactor—at high pressures to keep reactants in a liquid phase, with ensuing high energy consumption and operating costs.

Moreover, because of the introduction in the urea synthesis reactor of a high amount of water—for instance in the form of carbamate in aqueous solution—to facilitate the absorption of carbon dioxide in the ammonia solution and the subsequent reaction into carbamate, the $H_2O/CO_2$ molar ratio in such synthesis reactor is relatively high and the conversion yield is unsatisfactory.

A further drawback lies in the structural and operating complexity of the urea synthesis reactor necessary for implementing the above described process, which must include a special unit for the separation of inert gases (hydrogen and nitrogen) from carbon dioxide and from ammonia in the vapour phase.

According to this process of the prior art, there is also provided a step of condensation and separation of the ammonia produced by unreacted gases, typical of ammonia production processes, which is rather demanding from the economic and energy consumption viewpoints.

In U.S. Pat. Nos. 3,349,126, 4,012,443, 4,013,718, and 4,320,103, it is disclosed another type of process according to the prior art, which comprises a separate section for carbon dioxide absorption and carbamate synthesis.

According to this process, ammonia coming from the corresponding synthesis reactor is separated from unreacted gases—generally by absorption with water in a special absorption section—and sent to the carbamate synthesis section, wherein its reacts with the carbon dioxide contained in the synthesis raw gas flow coming from a reforming section, forming ammonia carbamate, which is sent to the urea synthesis reactor.

Also in this case, carbon dioxide absorption and the subsequent reaction into carbamate takes place in a milieu rich in water, which is then sent together with the carbamate to the urea synthesis reactor.

In addition, carbamate formation heat that is released during carbon dioxide absorption with the ammonia solution causes a strong evaporation of the latter, which involves the need of an additional recovery of ammonia at the outlet of the carbamate synthesis section, with ensuing problems of excessive dilution of the carbamate. At the same time, as the urea conversion reactor lacks carbamate formation heat, the operating conditions in said reactor become more difficult.

Otherwise said, according to this process of the prior art, producing carbamate outside the urea synthesis reactor involves not only the loss of the related formation heat, but also requires an addition of water, which is in contrast with the subsequent dehydration to urea, and therefore does not allow to obtain satisfactory conversion yields.

In conclusion, the processes for combined production of ammonia and urea according to prior art, besides requiring very complex plants for their implementation, and involving high investment and operating costs, as well as high energy consumption, do not allow in any case to obtain a high urea conversion yield due to the excessive $H_2O/CO_2$ molar ratio present in the corresponding synthesis reactor.

Because of these drawbacks, the above processes have not found till now a concrete application, in spite of the increasingly felt requirement in the field.

SUMMARY OF THE INVENTION

The problem underlying the present invention is to conceive a process for combined production of ammonia and urea, such as to allow on the one hand to obtain a high urea conversion yield, and to be, on the other hand, of simple implementation, with low operating and investment costs, and also with low energy consumption.

The above problem is solved, according to the invention, by a process of the aforesaid type, comprising the steps of:

submitting at least part of a flow comprising carbamate in aqueous solution coming from the urea recovery section to a partial decomposition treatment, to obtain a flow comprising ammonia and carbon dioxide in vapour phase and a flow comprising diluted carbamate in aqueous solution;

feeding said flow comprising ammonia and carbon dioxide in vapour phase to the urea synthesis reactor;

feeding said flow comprising diluted carbamate in aqueous solution resulting from said treatment step, a gas flow comprising hydrogen, nitrogen and carbon dioxide, preferably obtained by hydrocarbons steam reforming, and a flow comprising ammonia coming from the ammonia synthesis reactor to a carbamate synthesis section, reacting said ammonia with said carbon dioxide in said carbamate synthesis section, to obtain a flow comprising carbamate in aqueous solution and a gas flow comprising hydrogen and nitrogen;

feeding said flow comprising carbamate in aqueous solution to said urea synthesis reactor;

feeding said gas flow comprising hydrogen and nitrogen to said ammonia synthesis reactor.

Advantageously, thanks to the process according to the present invention, and in particular to the step of partial decomposition of the carbamate coming from the urea recovery section, it is possible to send to the carbamate synthesis section a water-rich solution, and to send at the same time to the urea synthesis reactor a flow comprising ammonia and substantially anhydrous carbon dioxide, which allows to reduce the $H_2O/CO_2$ molar ratio in such reactor increasing therefore the urea conversion yield.

In this way, besides keeping a low $H_2O/CO_2$ molar ratio in the urea synthesis reactor, it is also possible to advantageously exploit at least part of the water comprised in the carbamate in aqueous solution coming from the urea recovery section, recycling it in a simple and economical manner to the carbamate synthesis section, in order to facilitate carbon dioxide absorption and to keep the carbamate produced in the form of an aqueous solution, preventing so an undesired crystallisation of the same.

A further advantage resulting from the present process lies in the fact that by sending to the urea synthesis reaction a gas flow comprising ammonia and carbon dioxide, it is possible to supply at least part of the reaction heat necessary for urea synthesis directly from the heat generated by the reaction between ammonia and carbon dioxide in the urea synthesis reactor (carbamate formation heat). By so doing, it is possible to eliminate the problem of the heat balance in the urea synthesis reactor, even in those cases when substantially all of the carbon dioxide comprised in the synthesis raw gas is transformed into carbamate in the specific synthesis section.

Therefore, the process according to the present invention allows to obtain in an extremely simple and effective manner a combined ammonia and urea production at low investment and operating costs, and also with low energy consumption and a high urea conversion yield.

Differently from the processes according to the prior art, the present process advantageously allows also to eliminate the burdensome step of ammonia separation—by condensation or by absorption—from unreacted gases.

Actually, according to the present invention, ammonia and carbon dioxide are separated at the same time from the respective flows and caused to directly react in a single carbamate synthesis section by exploiting their high capacity of chemical reaction, obtaining a carbamate solution to be sent to the urea synthesis reactor.

Preferably, the flow coming from the ammonia synthesis reactor comprises ammonia in vapour phase, so that the ammonia carbamate synthesis can take place at least partly in the gas phase, with an extremely rapid reaction between ammonia and carbon dioxide, that does not require a prior absorption of carbon dioxide in the flow comprising ammonia.

If in the carbamate synthesis section a water amount should be required higher than the amount included in the diluted flow comprising carbamate in aqueous solution resulting from the treatment step, the process according to the present invention advantageously comprises the further step of feeding a flow comprising water coming from a urea concentration section to said carbamate synthesis section.

In this way, by recycling the water obtained in one of the sections downstream of the urea synthesis reactor, it is no longer necessary to send to the carbamate synthesis section a flow comprising water coming from outside the process, obtaining in this way a saving in operating costs.

In order to advantageously increase the urea conversion yield, the process according to the present invention further comprises the steps of:

submitting at least part of said flow comprising carbamate in aqueous solution obtained in said carbamate synthesis section to a partial decomposition treatment, to obtain a flow comprising ammonia and carbon dioxide in vapour phase and a flow comprising diluted carbamate in aqueous solution;

feeding said flow comprising ammonia and carbon dioxide in vapour phase to said urea synthesis reactor;

feeding said flow comprising diluted carbamate in aqueous solution resulting from said treatment step to said carbamate synthesis section.

In fact, by so doing it is possible to send to the urea synthesis section a substantially anhydrous flow comprising ammonia and carbon dioxide that allows to further reduce the $H_2O/CO_2$ molar ratio with the ensuing increase in the conversion yield, advantageously recycling to the carbamate synthesis section the water present in the carbamate flow coming from such section.

In order to control the temperature inside the urea synthesis reactor and to ensure optimum operating conditions for urea conversion, the process according to the present invention further comprises the steps of:

pre-heating a flow comprising recycled ammonia coming from a urea synthesis section; and feeding said pre-heated flow comprising ammonia to said urea synthesis reactor.

In accordance with an alternative embodiment of the process according to the present invention, the temperature inside the urea synthesis reactor is controlled thanks to the fact of further comprising the steps of:

cooling a flow comprising ammonia and carbon dioxide in vapour phase resulting from said carbamate partial decomposition treatment;

feeding the so cooled flow to said urea synthesis reactor.

Both of the above alternatives allow to exercise a direct and effective control of the temperature in the urea synthesis reactor, allowing to supply exactly the amount of heat necessary for a high conversion yield.

In the first case, the urea synthesis reactor is fed with a suitably pre-heated flow comprising recycled ammonia, while in the second case a flow comprising ammonia and carbon dioxide in vapour phase is suitably cooled before being fed to the urea synthesis reactor.

For the implementation of the aforesaid process, the invention advantageously provides a plant for combined production of ammonia and urea, comprising:

an ammonia synthesis reactor, a carbamate synthesis section, a urea synthesis reactor, a urea recovery section and a carbamate decomposition section;

means for feeding at least a part of a flow comprising carbamate in aqueous solution coming from said urea recovery section to said decomposition section;

means for feeding a flow comprising ammonia and carbon dioxide in vapour phase obtained in said decomposition section to said urea synthesis reactor;

respective means for feeding a flow comprising diluted carbamate in aqueous solution obtained in said decomposition section, a gas flow comprising hydrogen, nitrogen and carbon dioxide, coming preferably from a hydrocarbons steam reforming section, and a flow comprising ammonia coming from said ammonia synthesis reactor to said carbamate synthesis section;

means for feeding a flow comprising carbamate in aqueous solution obtained in said carbamate synthesis section to said urea synthesis reactor;

means for feeding a gas flow comprising hydrogen and nitrogen obtained in said carbamate synthesis section to said ammonia synthesis reactor.

According to a further aspect of the invention, there is also provided a method for the simultaneous modernization of an ammonia synthesis plant and a urea synthesis plant, comprising respectively an ammonia synthesis reactor and a urea synthesis reactor and a urea recovery section, characterized in that it comprises the steps of:

providing a carbamate synthesis section and a carbamate decomposition section;

providing means for feeding at least part of a flow comprising carbamate in aqueous solution coming from said urea recovery section to said decomposition section;

providing means for feeding a flow comprising ammonia and carbon dioxide in vapour phase obtained in said decomposition section to said urea synthesis reactor;

providing respective means for feeding a flow comprising diluted carbamate in aqueous solution obtained in said decomposition section, a gas flow comprising hydrogen, nitrogen and carbon dioxide, preferably coming from a hydrocarbons steam reforming section, and a flow comprising ammonia coming from said ammonia synthesis reactor to said carbamate synthesis section;

providing means for feeding a flow comprising carbamate in aqueous solution obtained in said carbamate synthesis section to said urea synthesis reactor;

providing means for feeding a gas flow comprising hydrogen and nitrogen obtained in said carbamate synthesis section to said ammonia synthesis reactor.

Thanks to the aforementioned method of modernization that combines an existing ammonia plant and an existing urea plant, it is possible to obtain—in a simple and economical way—a high urea conversion yield and at the same time drastic reductions in operating costs and energy consumption.

The characteristics and advantages of the inventions are set forth in the description of an embodiment thereof given below by way of non-limiting example with reference to the attached drawing.

SHORT DESCRIPTION OF THE DRAWING

FIG. 1 shows schematically a plant for combined production of urea and ammonia according to the invention, either realized ex novo or by modernizing an existing plant for ammonia production and an existing plat for urea production of conventional type.

DETAILED DESCRIPTION OF A PREFERRED EMBODIMENT

With the only aim of making the description of the present invention simpler, reference will be made to the connection ducts of the different plant parts, as well as to the same plant parts described in the following and represented in FIG. 1, conventional in themselves, only wherever it is strictly necessary.

With reference to FIG. 1, there is generally indicated by 1 a plant for combined production of ammonia and urea according to the invention.

Advantageously, plant 1 comprises an ammonia synthesis reactor 2, a carbamate synthesis section 3, a urea synthesis section 4, a urea recovery section 21, and a carbamate decomposition section 23.

The urea synthesis section 4 comprises, serially arranged relatively to one another, a urea synthesis reactor 5 and a high pressure (about 180 bar a) stripper 6, for the partial decomposition of carbamate and the separation of the free ammonia in aqueous solution present in the reaction mixture coming from reactor 5.

As will be seen later on, the process for combined production of ammonia and urea according to the present invention allows to obtain in the urea synthesis reactor 5 a yield comparable to the yield obtainable with the urea production plants according to the prior art, i.e. a yield comprised between 62% and 70%.

An example of operating conditions of the urea synthesis reactor 5 obtainable with the present invention are: $NH_3/CO_2$ molar ratio of 3.8, $H_2O/CO_2$ molar ratio of 0.8, 64% conversion yield, pressure 180 bar a, temperature 190° C.

In the example of FIG. 1, the part of the plant for urea production is of the total recycling type, i.e. with recycling of reactants to the synthesis reactor 5. However, the present invention is not limited to a particular type of urea synthesis process, but may be advantageously implemented also in plants that operate with urea synthesis processes for instance of the partial recycling type or of the "once through" type, without reactant recycling.

By 7, 8, 9a and 9b, there are indicated ducts for feeding a gas flow comprising hydrogen, nitrogen and carbon dioxide, a flow comprising ammonia, a flow comprising water, and a flow comprising diluted carbamate in aqueous solution, respectively, to the carbamate synthesis section 3.

The gas flow comprising hydrogen, nitrogen and carbon dioxide comes preferably from a hydrocarbons steam reforming section 10, comprising a primary reforming unit and a secondary reforming unit, not shown in FIG. 1 being of a conventional type and therefore known to those skilled in the art.

In the following of the description and the subsequent claims, with the term: "hydrocarbons", it is intended to generically mean a raw material which is the source of hydrogen and carbon, such as for instance methane or a mixture of liquid and/or gaseous hydrocarbons, such as natural gas and naphtha.

A gas flow comprising hydrocarbons and water steam is fed through duct 11 to the primary reforming unit of section 10, wherein a first hydrocarbons steam decomposition takes place that results in the formation of hydrogen, carbon monoxide and carbon dioxide. Then, decomposition is caused to go on in the secondary reforming step, wherein a gas flow comprising nitrogen (usually air) is also added.

By 12, 13 and 14 there are respectively indicated a desulfurisation section of the flow comprising hydrocarbons, a high temperature conversion section and a low temperature conversion section for the conversion of carbon monoxide into carbon dioxide.

Sections 12, 13 and 14 are of a conventional type and therefore they will not be described with more details in the following of the description.

For the purposes of the present invention, the gas flow comprising hydrogen, nitrogen and carbon dioxide fed through duct 7 to the carbamate synthesis section 3, may be produced by means of any other known technique, as an alternative to hydrocarbons steam reforming.

The flow comprising ammonia comes from the ammonia synthesis reactor 2 and is fed to section 3 through duct 8.

According to the example of FIG. 1, it is worth noting that duct 8 directly connects the ammonia synthesis reactor 2 to the carbamate synthesis section 3. In this way, it is possible to feed the latter section with a flow comprising free ammonia in vapour phase that reacts instantly with the carbon dioxide present in section 3, facilitating carbamate synthesis.

Advantageously, at least part of the water fed to the carbamate synthesis section 3 to spur the absorption of carbon dioxide and its immediate reaction with ammonia, is contained in the flow comprising diluted carbamate in aqueous solution coming—through duct 9b—from a carbamate decomposition section 23, which will be described with more details later on.

In the example of FIG. 1, a prefixed amount of water is also fed to the carbamate synthesis section through duct 9a. Such water—or part thereof—may come from a source outside plant 1 or, advantageously, from a urea concentration section 22.

However, feeding a flow comprising water through duct 9a is entirely optional, and serves mainly to increase the water content inside the carbamate synthesis section 3.

Actually, there is provided—but not represented—an embodiment of the invention wherein all water is fed to section 3 through duct 9b and comes from the carbamate decomposition section 23. According to a further embodiment of the invention—not represented—the carbamate synthesis section 3 is fed only through duct 9b, with additional water amounts coming from sources outside plant 1 or from the urea concentration section 22.

Preferably, about 30–40% of the total amount of water fed to the carbamate synthesis section 3 is fed through duct 9a, and about 60–70% (for instance 65%) is fed through duct 9b.

From the carbamate synthesis section 3, ducts 15 and 16 branch off for feeding a flow comprising carbamate in aqueous solution to the urea synthesis reactor 5 and a flow comprising hydrogen and nitrogen to the ammonia synthesis reactor 2, respectively.

Before being fed into the ammonia synthesis reactor 2, the gas flow comprising hydrogen and nitrogen is caused to pass—through duct 16—to a methanation section 17 and a drying section 18 of conventional type, where the gas flow is suitably purified.

In particular, in the methanation section 17, possible traces of carbon monoxide and/or carbon dioxide are suitably transformed into methane. In drying section 18, the gas flow comprising hydrogen and nitrogen is, on the contrary, dehydrated by washing it with liquid ammonia so as to remove possible water traces.

With regard to this, a flow comprising liquid ammonia is let into duct 16 through duct 19, and is then fed, together with the gas flow comprising hydrogen and nitrogen, to the drying section 18 which generally includes a gas/fluid separator.

In the separator, the water present in the gas flow is absorbed by ammonia so as to obtain an ammonia aqueous solution, which is advantageously recycled to the urea synthesis section 4 by means of ducts 20 and 25; at the same time, the water free gas flow comprising hydrogen and nitrogen is fed to the ammonia synthesis reactor 2 through duct 16.

The pressure and temperature operating conditions inside the ammonia synthesis reactor 2 are the typical ones of a conventional ammonia synthesis plant, well known to those skilled in the art.

Besides the synthesis section 4, the part of the plant for urea production also comprises a urea recovery section 21, a urea concentration section 22 and, advantageously, a carbamate decomposition section 23.

In the example of FIG. 1, the urea recovery section 21 is of the type comprising a carbamate decomposer 24 at a medium pressure (about 18 bar a), a carbamate decomposer 25 at low pressure (about 4 bar a) and an ammonia distillation column 26.

The urea concentration section 26 comprises in its turn a couple of vacuum stills 27 respectively 28 and a vacuum unit 29, shown by a broken line in FIG. 1.

The urea synthesis reactor 25 is connected—at a bottom end thereof and through ducts 15 and 30—with the carbamate synthesis section 3 and with duct 19 feeding a flow comprising ammonia, respectively.

Between the carbamate synthesis section 3 and the urea synthesis reactor 5, a separator 31 is provided to extract from the flow comprising carbamate in aqueous solution—through duct 32—possible hydrogen and nitrogen entrainments.

Reactor 5 is also connected—always at its bottom end and through duct 33—with stripper 6, from which there come a vapour phase (including ammonia, carbon dioxide and water steam) which is recycled to reactor 5 through duct 34 and a liquid phase (including a solution of partly purified urea) which is fed to the carbamate decomposer 24 of the urea recovery section 21 through duct 35.

Duct 35 passes through the urea concentration and recovery sections 21 and 22, so as to obtain at the output from still 28 of a purified urea flow which is sent—always through duct 35—to finishing apparatuses conventional in themselves and therefore not represented.

By 36 there are indicated ducts for feeding vapours comprising ammonia to the vacuum unit 29, wherein such vapours are condensed according to a well known method.

The obtained condensates, containing some residual ammonia in aqueous solution, are sent to a water treatment section (not represented) through duct 37.

According to a feature of the invention, duct 9a for feeding a flow comprising water to the carbamate synthesis section 3, is in fluid communication with duct 37 through duct 38 (represented by a broken line in FIG. 1).

In this way it is possible to feed the carbamate synthesis section 3 with a flow comprising water coming from the urea concentration section 22, thus advantageously recycling part of the water already present in the plant.

Vapours comprising water, ammonia and carbon dioxide, obtained in the carbamate decomposers 24 and 25 are sent—after being at least partly condensed—to the ammonia distillation column 26 which separates substantially pure ammonia from a carbamate aqueous solution.

The ammonia resulting from the distillation is condensed and at least partly recycled to the urea synthesis reactor 5 through ducts 19 and 30, and to the drying section 18 through ducts 19 and 16, respectively.

According to a particularly advantageous feature of the present invention, the flow comprising carbamate in aqueous solution coming out from the bottom of the ammonia distillation column 26 is sent—through duct 39—to the carbamate decomposition section 23. In this way, there is obtained a substantially anhydrous flow comprising ammonia and carbon dioxide in vapour phase which is recycled to the urea synthesis reactor 5 through ducts 40 and 34, and a very diluted flow of carbamate in aqueous solution which is advantageously recycled to the carbamate synthesis section 3 through duct 9b.

Advantageously, in accordance with the process for combined production of ammonia and urea of this invention, at least part of a flow comprising carbamate in aqueous solution coming (duct 39) from the urea recovery section 21 is submitted to a partial decomposition treatment resulting in the production of a flow comprising ammonia and carbon dioxide in vapour phase and a flow comprising diluted carbamate in aqueous solution. The flow comprising ammonia and carbon dioxide in vapour phase is fed (ducts 40, 34) to the urea synthesis reactor 5, while the flow comprising diluted carbamate in aqueous solution together with a gas flow comprising hydrogen, nitrogen and carbon dioxide and a flow comprising ammonia coming from an ammonia synthesis reactor 25 are fed (ducts 9b, 7 and 8) to a carbamate synthesis section, where ammonia and carbon dioxide are reacted to obtain a flow comprising carbamate in aqueous solution and a gas flow comprising hydrogen and nitrogen. The flow comprising carbamate in aqueous solution is then fed (duct 15) to a urea synthesis reactor 5, while the gas flow comprising hydrogen and nitrogen is fed (duct 16) to the ammonia synthesis reactor 2.

Thanks to the present invention, it is possible to control—and to keep at low levels—the amount of water sent to the urea synthesis reactor 5, which is advantageously recycled to the carbamate synthesis section 3, allowing in this way—in a simple and effective manner—to obtain high urea conversion yields.

Otherwise said, the step of partial decomposition of carbamate allows a high process flexibility, as it allows to operate even with large water amounts in the carbamate synthesis section 3, without for this affecting adversely the $H_2O/CO_2$ molar ratio in the urea synthesis reactor 5, and therefore the conversion yield.

According to a particularly advantageous embodiment of the present invention, it is possible to further reduce the $H_2O/CO_2$ molar ratio in the urea synthesis reactor 5, increasing consequently the conversion yield, by feeding at least a part of the flow comprising carbamate in aqueous solution coming from section 3 to the carbamate decomposition section 23 through duct 41 (represented by the broken line in FIG. 1), obtaining a substantially anhydrous flow comprising ammonia and carbon dioxide in vapour phase which is sent to the urea synthesis reactor 5 through ducts 40 and 34, and a very diluted flow of carbamate in aqueous solution which is advantageously recycled to the carbamate synthesis section 3 through duct 9b.

As a consequence, the process for the combined production of ammonia and urea is further characterized in that at least part of the flow comprising carbamate in aqueous solution coming (duct 15) from the carbamate synthesis section 3 is advantageously submitted to a partial decomposition treatment to obtain a flow comprising ammonia and carbon dioxide in vapour phase and a flow comprising diluted carbamate in aqueous solution which is sent (ducts 40, 34) to the urea synthesis reactor 5, and to (duct 9b) the carbamate synthesis section 3, respectively.

Advantageously, depending on the water content of the flows comprising carbamate in aqueous solutions coming from sections 3 and 21, more or less great parts of such flows are sent to the carbamate decomposition section 23, so as to obtain a recycling of water to the carbamate synthesis section 3 and to send to the urea synthesis reactor 5 substantially anhydrous reactants.

The partial decomposition of the carbamate comprised in the flow coming out from the carbamate synthesis section 3 and in the flow coming out from the urea recovery section 21, respectively, can take place in two separate decomposition units or—as shown in FIG. 1—in a single decomposition unit forming section 23.

Preferably, the carbamate decomposition section 23 operates at the same pressure and temperature conditions of stripper 6, which are also the same of the urea synthesis reactor 5.

According to a particularly advantageous point of the present invention, the carbamate synthesis section 3 comprises three chambers 42, 43 and 44 separated by two film absorbers 45 and 46.

In the example of FIG. 1, chambers 42–44 and film absorbers 45–46 are comprised within a single substantially vertical tubular device.

The first chamber 42 is located in a bottom end of section 3, and is in fluid communication with duct 7 feeding the gas flow comprising hydrogen, nitrogen and carbon dioxide to the carbamate synthesis section 3, respectively with duct 15 feeding the flow comprising carbamate in aqueous solution obtained in the carbamate synthesis section 3 to the urea synthesis reactor 5.

The second chamber 45 is located in a central part of section 3, and is in fluid communication with duct 8 feeding a flow comprising ammonia coming from the ammonia synthesis reactor 2 to the carbamate synthesis section 3.

The third chamber 44 is located at a the top end of section 3, and is in fluid communication with ducts 9a and 9b feeding a flow comprising water respectively diluted carbamate in aqueous solution to the carbamate synthesis section 3, and with duct 16 feeding a gas flow comprising hydrogen and nitrogen obtained in the carbamate synthesis section 3 to the ammonia synthesis reactor 2.

The first film absorber 45 is located between the first and the second chambers 42, 43, and comprises a plurality of tubes having opposed ends in fluid communication with the first respectively the second chamber.

The second film absorber 46 is located between the second and the third chambers 43, 44, and comprises a plurality of tubes having opposed ends in fluid communication with the second respectively the third chamber.

Thanks to a so structured carbamate synthesis section 3, it is possible to obtain a rapid and effective reaction between carbamate and carbon dioxide in a small size, structurally simple device involving low realisation and operating costs.

The flow comprising diluted carbamate in aqueous solution coming from the urea recovery section 21 is preferably fed to the third chamber 44—through duct 9b—close to the second film absorber 46.

Moreover, particularly satisfactory results have been obtained by feeding said flow comprising diluted carbamate in aqueous solution to the third chamber 44, close to the top end of the carbamate synthesis section 3, as represented in FIG. 1 by the broken line.

In the same way, the flow comprising water is fed to the third chamber 44—through duct 9a—close to the top end of the carbamate synthesis section 3.

Advantageously, the third chamber 44—which operates preferably in adiabatic conditions—comprises a plurality of horizontal perforated plates of a conventional type, which allow to increase the absorption yield.

In accordance with the particular structure of the carbamate synthesis section 3 of FIG. 1, the flow comprising hydrogen, nitrogen and carbon dioxide coming from the hydrocarbons steam reforming section 10 is fed—through duct 7—to the first chamber 42.

From chamber 42, said flow is caused to enter—tube side—into the first film absorber 45, wherein it flows in countercurrent with a flow comprising ammonia and carbamate in aqueous solution coming from the second chamber 43.

In this part, most of the carbon dioxide reacts with the free ammonia—preferably either in vapour or in liquid form—forming carbamate that collects in chamber 42.

An example of composition of the flow comprising carbamate in aqueous solution leaving chamber 42—obtainable with the process according to the present invention—is the following one: ammonia 37.7% by weight, carbon dioxide 43.7% by weight, and water 19.0% by weight.

The gas flow leaving the first film absorber 45 mixes—in chamber 43—with the ammonia flow coming from the ammonia synthesis reactor 2 through duct 8, and enters—tube side—into the second film absorber 46, wherein most of the carbon dioxide and the ammonia in vapour phase are absorbed by an ammonia diluted solution coming from the third chamber 44.

The third chamber 44, which is fed through ducts 9a and 9b by a flow comprising water coming from the urea concentration section 22, respectively by a flow comprising carbamate in aqueous solution coming from the urea recovery section 21, allows the final removal of residual ammonia and carbon dioxide.

Thanks to the present invention, it is for instance possible to obtain a gas flow comprising hydrogen and nitrogen coming out of chamber 44 (duct 16) having a content of residual ammonia equal to about 1% mol, and of residual carbon dioxide equal to about 0.05% mol.

The reaction heat that develops in the carbamate synthesis section 3 is advantageously removed by indirect heat exchange with a cooling fluid (for instance water) which is preferably caused to pass shell side in the film absorbers 45 and 46.

In this way, it is possible to keep the temperature inside the carbamate synthesis section 3 within a range of values such as to prevent any carbamate crystallisation in the tubes of the film absorbers 45 and 46.

Optimum pressure and temperature values inside the carbamate synthesis section 3 are for instance comprised between 140 and 200 bar a (preferably 180 bar a) and between 110 and 150° C. (preferably 130° C.), respectively.

The exhaust gas rich in inert substances such as nitrogen and methane coming out of the ammonia synthesis reactor 2 is suitably separated from the reacted gas and washed in a washing section 47 with the flow comprising water fed to the carbamate synthesis section 3 through duct 9a. Once washed, the exhaust gas is sent to a recovery plant of conventional type (not represented).

By so doing, it is possible to recover—through the washing water—most of the ammonia entrained in the exhaust gas, which is advantageously fed to the carbamate synthesis section 3.

By 50 there is represented a cooling apparatus that allows to cool the flow comprising ammonia coming from the synthesis reactor 2 to values lower than about 100° C.

According to a particularly advantageous feature of the present invention, there are provided in the plant for combined production of ammonia and urea, means for cooling the gas flow comprising hydrogen, nitrogen and carbon dioxide by indirect heat exchange with a flow comprising urea in aqueous solution in the urea recovery section 21.

In particular, as shown in FIG. 1, the gas flow comprising hydrogen, nitrogen and carbon dioxide coming from the reforming section 10 is caused to pass—by means of duct 7—through the carbamate decomposers 24 and 25 of the urea recovery section 21, wherein it cools by indirect heat exchange with the partly purified urea flow.

In this way, there is advantageously obtained the double aim of cooling, on the one hand, the gas flow coming from the reforming section 10 to be fed to the carbamate synthesis section 3, and to supply, on the other hand, the heat necessary for the decomposition of the carbamate comprised in the partly purified urea flow, without the need of having recourse to external heat sources, which therefore results in remarkable savings from the points of view of energy consumption and operating costs.

According to another feature of the present invention, the urea synthesis reaction temperature is advantageously controlled by feeding reactor 5 with a suitably pre-heated ammonia comprising flow.

To this aim, the plant for combined production of ammonia and urea is further provided with means (shown in FIG. 1 by the heat exchanger 48) for pre-heating a flow comprising recycled ammonia coming—through ducts 29 and 30—from the urea recovery section 21, and means (duct 30) for feeding the so heated ammonia comprising flow to the urea synthesis reactor 5.

If not negligible amounts of ammonia and carbon dioxide are sent to the urea synthesis reactor 5, the reaction temperature control is no longer performed (only) by pre-heating a flow comprising ammonia, but by suitably cooling the flow comprising ammonia and carbon dioxide.

In fact, in this case, the heat necessary for the urea synthesis reaction is supplied at least partly by the formation heat of the carbamate produced within reactor 5.

As a consequence, depending on the amount of ammonia and carbon dioxide fed to reactor 5, it may be necessary to supply additional heat through the heat exchanger 48, or to reduce the heat inside reactor 5 by removing excess heat.

The latter possibility takes place generally when, besides stripper 6 of the urea synthesis section 4, the carbamate decomposition section 23 is also provided.

In this case, the plant according to the present invention advantageously includes means (represented in FIG. 1 by the heat exchanger 49) for cooling a flow comprising ammonia and carbon dioxide in vapour phase coming from a carbamate decomposition section (reference numerals 6 and 23), and means (ducts 40 and 34) for feeding the so cooled flow to the urea synthesis reactor 5.

A water flow is preferably utilised as a cooling fluid, so as to produce recovery steam at high thermal level, for instance 5 bar a.

The plant of FIG. 1 may be a new plant or it may be realized by modernizing an existing plant for ammonia production and an existing plant for urea production.

According to the present invention, a method for the simultaneous modernization of an ammonia synthesis plant and a urea synthesis plant comprising respectively an ammonia synthesis reactor (2), a urea synthesis reactor (5), and a urea recovery section (21) advantageously comprises the steps of providing, respectively, a carbamate synthesis section (3) and a carbamate decomposition section (23), means for feeding at least a part of a flow comprising carbamate in aqueous solution coming from said urea recovery section (21) to said decomposition section, means (40, 34) for feeding a flow comprising ammonia and carbon dioxide in vapour phase obtained in said decomposition section to said urea synthesis reactor (5), respective means (9*b*, 7 and 8) for feeding a flow comprising diluted carbamate in aqueous solution obtained in said decomposition section, a flow comprising hydrogen, nitrogen and carbon dioxide, preferably coming from a hydrocarbons steam reforming section, and a flow comprising ammonia coming from said ammonia synthesis reactor (2) to said carbamate synthesis section (3), means (15) for feeding a flow comprising carbamate in aqueous solution obtained in said carbamate synthesis section (3) to said urea synthesis reactor (5), and means (16) for feeding a gas flow comprising hydrogen and nitrogen obtained in said carbamate synthesis section (3) to said ammonia synthesis reactor (2).

Moreover, according to further embodiments of said method of modernization according to the invention, further sections or means are advantageously provided, as described in dependent claims 12–16 appended hereto.

In the present description and subsequent claims, with the term: "means for feeding", it is generally intended to mean the various parts of a plant, such as for instance ducts, pumps and compressors, that serve to transport a liquid or gaseous fluid from one to another part of the plant.

From the foregoing description emerge clearly the numerous advantages achieved by the present invention; in particular, it is obtained a process for combined production of ammonia and urea at high yield, of simple implementation, with low investment and operating costs and with low energy consumption.

What is claimed is:

1. Plant for combined production of ammonia and urea comprising:

an ammonia synthesis reactor (2), a carbamate synthesis section (3), a urea synthesis reactor (5), a urea recovery section (21) and a carbamate decomposition section (23);

means (39) for feeding at least a part of a flow comprising carbamate in aqueous solution coming from said urea recovery section (21) to said decomposition section (23) without connecting said ammonia synthesis reactor (2), said carbamate synthesis section (3) and said urea synthesis reactor (5);

means (40, 34) for feeding a flow comprising ammonia and carbon dioxide in vapor phase obtained in said decomposition section (23) to said urea synthesis reactor (5);

means (9*b*) for feeding a flow comprising diluted carbamate in aqueous solution obtained in said decomposition section (23) to said carbamate synthesis section (3), without connecting said ammonia synthesis reactor (2), said urea synthesis reactor (5) and said urea recovery section (21);

respective means (7 and 8) for feeding a gas flow comprising hydrogen, nitrogen and carbon dioxide, and a flow comprising ammonia coming from said ammonia synthesis reactor (2) to said carbamate synthesis section (3);

means (15) for feeding a flow comprising carbamate in aqueous solution obtained in said carbamate synthesis section (3) to said urea synthesis reactor (5);

means (16) for feeding a gas flow comprising hydrogen and nitrogen obtained in said carbamate synthesis section (3) to said ammonia synthesis reactor (2).

2. Plant according to claim 1, characterized in that it further comprises means (9*a*) for feeding a flow comprising water to said carbamate synthesis section (3), in fluid communication with a urea concentration section (22).

3. Plant according to claim 1, characterized in that said carbamate synthesis section (3) comprises:

a first chamber (42) in fluid communication with said means (7) for feeding a gas flow comprising hydrogen, nitrogen and carbon dioxide to said carbamate synthesis section (3), and with said means (15) for feeding a flow comprising carbamate in aqueous solution obtained in said carbamate synthesis section (3) to said urea synthesis reactor (5), respectively;

a second chamber (43) in fluid communication with said means (8) for feeding a flow comprising ammonia coming from said ammonia synthesis reactor (2) to said carbamate synthesis section (3);

a third chamber (44) in fluid communication with said means (9*b*) for feeding a flow comprising diluted carbamate in aqueous solution to said carbamate synthesis section (3), and with said means (16) for feeding a gas flow comprising hydrogen and nitrogen obtained in said carbamate synthesis section (3) to said ammonia synthesis reactor (2), respectively;

a first film absorber (45) located between said first and said second chamber (42, 43) and comprising a plurality of tubes having opposed ends in fluid communication with said first and said second chamber (42, 43);

a second film absorber (46) located between said second and said third chamber (43, 44) and comprising a plurality of tubes having opposed ends in fluid communication with said second and said third chamber (43, 44).

4. Plant according to claim 3, characterized in that said third chamber (44) is in fluid communication with means (9a) for feeding a flow comprising water coming from a urea concentration section (22).

5. Plant according to claim 3, characterized in that said chambers (42–44) and said absorbers (45–46) are comprised in a single substantially vertical tubular device, the first chamber (42) and the third chamber (44) being located in a bottom respective to a top end of said device.

6. Plant according to claim 1, characterized in that said means (8) for feeding the flow comprising ammonia directly connect said ammonia synthesis reactor (2) to said carbamate synthesis section (3).

7. Plant according to claim 1, characterized in that it further comprises means (24, 25) for cooling said flow comprising hydrogen, nitrogen and carbon dioxide by indirect heat exchange with a flow comprising urea in aqueous solution in said urea recovery section (21).

8. Plant according to claim 1, characterized in that is further comprises:

means (41) for feeding at least part of said flow comprising carbamate in aqueous solution coming from said carbamate synthesis section (3) to said carbamate decomposition section (23).

9. Plant according to claim 8, characterized in that it further comprises:

means for cooling said flow comprising ammonia and carbon dioxide in vapor phase coming from said carbamate decomposition section; and means for feeding said cooled flow to said urea synthesis reactor.

10. Plant according to claim 1, characterized in that it further comprises:

means (48) for pre-heating a flow comprising recycled ammonia coming from said urea recovery section (21); and means (30) for feeding said heated flow comprising ammonia to said urea synthesis reactor (5).

11. Plant according to claim 1, characterized in that it further comprises:

means (49) for cooling said flow comprising ammonia and carbon dioxide in vapor phase coming from said carbamate decomposition section (23);

means (34) for feeding said cooled flow to said urea synthesis reactor (5).

12. Method for the simultaneous modernization of a plant for ammonia synthesis and a plant for urea synthesis, comprising respectively an ammonia synthesis reactor (2) and a urea synthesis reactor (5) and a urea recovery section (21), characterized in that it comprises the steps of:

providing a carbamate synthesis section (3) and a carbamate decomposition section (23);

providing means (39) for feeding at least part of a flow comprising carbamate in aqueous solution coming from said urea recovery section (21) to said decomposition section (23), without connecting said ammonia synthesis reactor (2), said carbamate synthesis section (3) and said urea synthesis reactor (5);

providing means (40, 34) for feeding a flow comprising ammonia and carbon dioxide in vapor phase obtained in said decomposition section (23) to said urea synthesis reactor (5);

providing means (9b) for feeding a flow comprising diluted carbamate in aqueous solution obtained in said decomposition section (23) to said carbamate synthesis section (3), without connecting said ammonia synthesis reactor (2), said urea synthesis reactor (5) and said urea recovery section (21);

providing respective means (7 and 8) for feeding a gas flow comprising hydrogen, nitrogen and carbon dioxide, and a flow comprising ammonia coming from said ammonia synthesis reactor (2) to said carbamate synthesis section (3);

providing means (15) for feeding a flow comprising carbamate in aqueous solution obtained in said carbamate synthesis section (3) to said urea synthesis reactor (5);

providing means (16) for feeding a gas flow comprising hydrogen and nitrogen obtained in said carbamate synthesis section (3) to said ammonia synthesis reactor (2).

13. Method of modernization according to claim 12, characterized in that said carbamate synthesis section comprises:

a first chamber (42) in fluid communication with said means (7) for feeding a gas flow comprising hydrogen, nitrogen and carbon dioxide to said carbamate synthesis section (3), and with said means (15) for feeding a flow comprising carbamate in aqueous solution obtained in said carbamate synthesis section (3) to said urea synthesis reactor (5), respectively;

a second chamber (43) in fluid communication with said means (8) for feeding a flow comprising ammonia coming from said ammonia synthesis reactor (2) to said carbamate synthesis section (3);

a third chamber (44) in fluid communication with said means (9b) for feeding a flow comprising diluted carbamate in aqueous solution to said carbamate synthesis section (3), and with said means (16) for feeding a gas flow comprising hydrogen and nitrogen obtained in said carbamate synthesis section (3) to said ammonia synthesis reactor (2), respectively;

a first film absorber (45) located between said first and said second chamber (42, 43) and comprising a plurality of tubes having opposed ends in fluid communication with said first and said second chamber (42, 43);

a second film absorber (46) located between said second and said third chamber (43, 44) and comprising a plurality of tubes having opposed ends in fluid communication with said second and said third chamber (43, 44).

14. Method of modernization according to claim 12, characterized in that it further comprises the step of providing means (24, 25) for cooling said flow comprising hydrogen, nitrogen and carbon dioxide by indirect heat exchange with a flow comprising urea in aqueous solution in said urea recovery section (21).

15. Method of modernization according to claim 12, characterized in that it further comprises the step of:

provicing means (41) for feeding at least part of said flow comprising carbamate in aqueous solution coming from said carbamate synthesis section (3) to said carbamate decomposition section (23).

16. Method of modernization according to claim 12, characterized in that it further comprises the steps of:

providing means (48) for pre-heating a flow comprising recycled ammonia coming from a urea recovery section (21); and providing means (30) for feeding said heated flow comprising ammonia to said urea synthesis reactor (5).

17. Method of modernization according to claim 12, characterized in that it further comprises the steps of:

providing means (49) of cooling said flow comprising ammonia and carbon dioxide in vapor phase coming from said carbamate decomposition section (23);

providing means (34) for feeding the cooled flow to said urea synthesis reactor (5).

\* \* \* \* \*